United States Patent [19]

Weltzin

[11] Patent Number: 5,534,411
[45] Date of Patent: Jul. 9, 1996

[54] MONOCLONAL IGA ANTIBODY SPECIFIC FOR RESPIRATORY SYNCYTIAL VIRUS, A HYBRIDOMA CELL LINE THAT PRODUCES THIS ANTIBODY AMD METHODS OF USING THE ANTIBODY TO DIAGNOSE RSV INFECTION

[75] Inventor: Richard A. Weltzin, Lunenburg, Mass.

[73] Assignee: OraVax, Inc., Cambridge, Mass.

[21] Appl. No.: 411,858

[22] Filed: Mar. 28, 1995

Related U.S. Application Data

[63] Continuation of Ser. No. 99,477, Jul. 30, 1993, abandoned.
[51] Int. Cl.$^6$ .......................... G01N 33/53; C07K 16/08; C12N 5/20
[52] U.S. Cl. .................... 435/7.2; 435/240.27; 435/7.94; 435/70.21; 435/172.2; 530/388.3; 530/391.1; 530/391.3; 436/548
[58] Field of Search .............................. 530/388.3, 391.1, 530/391.3; 435/7.2, 7.94, 240.27, 70.21, 172.2; 436/548

[56] References Cited

U.S. PATENT DOCUMENTS 4,800,078  1/1989  Prince et al. .
5,223,254  6/1993  Paradiso et al. .

FOREIGN PATENT DOCUMENTS 2040770    4/1991   Canada .
0380068A1  8/1990   European Pat. Off. .
745523     6/1978   U.S.S.R. .
WO91/16074 10/1991  WIPO .
WO92/01473 2/1992   WIPO .
WO92/04381 3/1992   WIPO .
WO93/11795 6/1993   WIPO .

OTHER PUBLICATIONS

Barbas III et al., Human Monoclonal Fab Fragments Derived from a Combinatorial Library Bind to Respiratory Syncytial Virus F Glycoprotein and Neutralize Infectivity, Proc. Natl. Acad. Sci. USA 89:10164–10168, 1992.

Fischer, Therapeutic Uses of Intravenous Gammaglobulin for Pediatric Infections, Pediatric Clinics of North America 35:517–533, 1988.

Groothuis and Simoes, Immunoprophylaxis and Immunotherapy: Role in the Prevention and Treatment of Respiratory Syncytial Virus, International J. Antimicrobial Agents 2:97–103, 1993.

Groothuis et al., Prophylactic Administration of Respiratory Syncytial Virus Immune Globulin to High–Risk Infants and Young Children, N. Engl. J. Med. 329:1524–30, 1993.

Kennedy et al., Production and Characterization of Bovine Monoclonal Antibodies to Respiratory Syncytial Virus, J. Gen. Virol. 69:3023–3032, 1988.

Taylor et al., Monoclonal Antibodies Protect Against Respiratory Syncytial Virus, The Lancet II:976, 1983.

Nandapalan et al., Mammary and Serum Antibody Levels to RS Virus in Mothers Exposed to Respiratory Syncytial Virus, Sixth International Congress of Virology Abstracts 260:P36–2, 1984.

Okamoto et al., Effect of Breast Feeding on the Development of Anti–Idiotype Antibody Response to F . . . Syncytial Virus In Infant Mice After Post–Partum Maternal Immunization, J. Immunology 142:2507–2512, 1989.

Piazza et al., Immunotherapy of Respiratory Syncytial Virus Infection in Cotton Rats (*Sigmodon fulviventer*) Using IgG in a Small[\N]Particle Aerosol, J. Infectious Diseases 166:1422–1444, 1992.

Prince et al., Effectiveness of Topically Administered Neutralizing Antibodies in Experimental Immunotherapy of Respiratory Syncytial Virus Infection in Cotton Rats, J. Virology 61:1851–1854, 1987.

Prince et al., Mechanisms of Immunity to Respiratory Syncytial Virus in Cotton Rats, Infection and Immunity 42:81–87, 1983.

Russell et al., Principles of Antibody Therapy, British Medical Journal 305:1424–1429, 1992.

Suffin et al., Immunoprophylaxis of Respiratory Syncytial Virus Infection in the Infant Ferret, J. Immunol. 123:10–14, 1979.

Taylor et al., Humanised Monoclonal Antibody to Respiratory Syncytial Virus, The Lancet 337:1411–1412, 1991.

Tempest et al., Reshaping a Human Monoclonal Antibody to Inhibit Human Respiratory Syncytial Virus Infection In Vivo, Bio/Technology 9:266–271, 1991.

Trudel et al., Protection of BALB/c Mice from Respiratory Syncytial Virus Infection by Immunization with a Synthetic Peptide Derived from the G Glycoprotein, Virology 185:749–757, 1991.

Walsh and Hruska, Monoclonal Antibodies to Respiratory Syncytial Virus Proteins: Identification of the Fusion Protein, J. Virology 47:171–177, 1983.

Beeler et al., "Neutralization Epitopes of the F Glycoprotein of Respiratory Syncytial Virus: Effect of Mutation upon Fusion Function", Journal of Virology 63:2941–2950, 1989.

Belshe et al., "Parenteral Adminstration of Live Respiratory Syncytial Virus Vaccine: Results of a Field Trial", The Journal of Infectious Diseases 145:311–319, 1982.

Brideau et al., "Protection of Cotton Rats against Human Respiratory Syncytial Virus by Vaccination with a Novel Chimeric FG Glycoprotein", J. Gen. Virol. 70:2637–2644, 1989.

Bruhn et al., "Respiratory Syncytial Virus in Early Infancy", Am J Dis Child 131:145–148, 1977.

(List continued on next page.)

*Primary Examiner*—Paula K. Hutzell
*Attorney, Agent, or Firm*—Fish & Richardson

[57] ABSTRACT

A new hybridoma cell line HNK20 which secretes a monoclonal IgA antibody to respiratory syncytial virus is disclosed. The antibody has diagnostic uses in respect of Respiratory Syncytial Virus.

9 Claims, 5 Drawing Sheets

OTHER PUBLICATIONS

Collins et al., "Evaluation in chimpanzees of vaccinia virus recombinants that express the surface glycoproteins of human respiratory syncytial virus", Vaccine 8:164–168, 1990.

Connors et al., "Respiratory Syncytial Virus (RSV) F, G, M2 (22K), and N Proteins Each Induce Resistance to RSV Challenge, but Resistance . . . N Proteins Is Relatively Short–Lived", J. Virology 65:1634–1637, 1991.

Connors et al., "Cotton rats previously immunized with a chimeric RSV FG glycoprotein develop enhanced pulmonary pathology when infected with RSV, . . . " Vaccine 10:475–484, 1992.

Elango et al, "Resistance to human respiratory syncytial virus (RSV) infection induced by immunization of cotton rats with a recombinant . . . " Proc. Natl. Acad. Sci. USA 83:1906–1910, 1986.

Fenner, "The Classification and Nomenclature of Viruses Summary of Results of Meetings of the International Committee on Taxonomy of Viruses in Madrid, Sep. 1975", Virology, 71:371–378, 1976.

Garcia–Barreno et al., "Marked Differences in the Antigenic Structure of Human Respiratory Syncytial Virus F and G Glycoproteins", Journal of Virology 63:925–932 Feb. 1989.

Glezen et al., "Risk of Primary Infection and Reinfection With Respiratory Syncytial Virus", 140:543–546, 1986.

Graman et al., "Epidemiology and Control of Nosocomial Viral Infections", Infectious Diseases Clinics of North America 3:815–841, 1989.

Groothuis et al., "Use of Intravenous Gamma Globulin To Passively Immunize High–Risk Children against . . . Virus: Safety and Pharmacokinetics", Antimicrobial Agents and Chemotherapy 35:1469–1473, 1991.

Hall et al., "Immunity to and Frequency of Reinfection with Respiratory Syncytial Virus", The Journal of Infectious Diseases 163:693–698, 1991.

Hall et al., "Modes of transmission of respiratory syncytial virus", The Journal of Pediatrics 99:100–103, 1981.

Hemming et al., "Intravenous immunoglobulin G in viral respiratory infections for newborns and infants", 5:S204–S206, 1986.

Huang et al., "The Genome of Respiratory Syncytial Virus is a Negative–Stranded RNA That Codes for at Least Seven mRNA Species", Journal of Virology, 43:150–157, 1982.

Johnson et al., "The G glycoprotein of human respiratory syncytial viruses of subgroups A and B: Extensive sequence divergence between antigenically . . . ", Proc. Natl. Acad. Sci. USA 84:5625–5629, 1987.

Kanesaki et al., "Effectiveness of Enteric Immunization in the Development of Secretory Immunoglobulin A Response and the Outcome of Infection . . . ", Journal of Virology 65:657–663, 1991.

Kapikian et al., "An Epidemiologic Study of Altered Clinical Reactivity to Respiratory Syncytial (RS) Virus Infection in Children Previously . . . ", American Journal of Epidemiology 89:405–421, 1969.

Kaul et al., "Secretory Antibody Response to Respiratory Syncytial Virus Infection", Am. J. Dis. Child, 135:1013–1016, 1981.

Kauppi et al., "Anti–Capsular Polysaccharide Antibodies Reduce Nasopharyngeal Colonization by Haemophilus influenzae Type b in Infant Rats", The Journal of Infectious Diseases 167:365–371, 1993.

Kim et al., "Safety and Antigenicity of Temperature Sensitive (TS) Mutant Respiratory Syncytial Virus (RSV) in Infants and Children", Pediatrics 52:56/72–63/79, 1973.

King et al., "Recombinant Vaccinia Viruses Carrying the N Gene of Human Respiratory Syncytial Virus: Studies of Gene Expression in Cell . . . ", Journal of Virology 61:2885–2890, 1987.

Köhler et al., "Fusion between immunoglobulin–secreting and nonsecreting myeloma cell lines", Eur. J. Immunol. 6:292–295, 1976.

Lopez et al., "Location of a Highly Conserved Neutralizing Epitope in the F Glycoprotein of Human Respiratory Syncytial Virus", Journal of Virology 64:927–930, 1990.

McIntosh et al., "Respiratory Syncytial Virus", Virology, Second Edition, Chapter 38, pp. 1045–1072, 1990.

McIntosh et al., "The Immunologic Response to Infection with Respiratory Syncytial Virus in Infants", The Journal of Infectious Diseases 138:24–32, 1978.

McIntosh et al., "Attenuated Respiratory Syncytial Virus Vaccines in Asthmatic Children", Pediatric Research, 8:689–696, 1974.

Mills et al., "Experimental Respiratory Syncytial Virus Infection of Adults", The Journal of Immunology, 107:123–130, 1971.

Murphy et al., "Enhanced pulmonary histopathology is observed in cotton rats immunized with formalin–inactivated respiratory syncytial virus (RSV) . . . ", Vaccine 8:497–502, 1990.

Norrby et al., "Site–directed serology with synthetic peptides representing the lage glycoprotein G of respiratory syncytial virus", Proc. Natl. Acad. Sci. USA 84:6572–6576, 1987.

Olmsted et al., "Expression of the F glycoprotein of respiratory syncytial virus by a recombinant vaccinia virus: Comparison of the individual . . . " Proc. Natl. Acad. Sci. USA 83:7462–7466, 1986.

Olmsted et al., "Evaluation in non–human primates of the safety, immunogenicity and efficacy of recombinant vaccinia viruses . . . ", Vaccine 6:519–524, 1988.

Paradiso et al., "Mapping of a fusion related epitope of the respiratory syncytial virus fusion protein", Vaccine 9:231–237, 1991.

Prince et al., "Enhancement of Respiratory Syncytial Virus Pulmonary Pathology in Cotton Rats by Prior Intramuscular Inoculation . . . ", Journal of Virology 57:721–728, 1986.

Reuman et al., "Rapid Recovery in Mice After Combined Nasal/Oral Immunization With Killed Respiratory Syncytial Virus", Journal of Medical Virology 32:67–72, 1990.

Routledge et al., "The Purification of Four Respiratory Syncytial Virus Proteins and Their Evaluation as Protective Agents . . . ", J. Gen. Virol. 69:293–303, 1988.

Scott et al., "Respiratory syncytial virus neutralizing activity in nasopharygenal secretions", J. Hyg., Camb. 68:581–588, 1970.

Soman et al., "Purification and Characterization of Murine Monoclonal IgA Against *Vibrio Cholerae*.", Mucosal Immunology II 150:, Part II, p. 116A/653, 1993.

Stott et al., "Human Respiratory Syncytial Virus Glycoprotein G Expressed from a Recombinant Vaccinia Virus Vector Protects . . . ", Journal of Virology 60:607–613, 1986.

Taylor et al., "Monoclonal antibodies protect against respiratory syncytial virus infection in mice", Immunology 52:137–142, 1984.

Trudel et al., "Identification of a Synthetic Peptide as Part of a Major Neutralization Epitope of Respiratory Syncytial Virus", J. Gen. Virol. 68:2273–2280, 1987.

Walsh et al., "Purification and Characterization of the Respiratory Syncytial Virus Fusion Protein", J. Gen. Virol. 66:409–415, 1985.

Walsh et al., "Purification and Characterization of GP90, One of the Envelope Glycoproteins of Respiratory Syncytial Virus", J. Gen. Virol. 65:761–767, 1984.

Walsh et al., "Immunization with Glycoprotein Subunits of Respiratory Syncytial Virus to Protect Cotton Rats Against Viral Infection", The Journal Infectious Diseases 155:1198–1204, 1987.

Walsh et al., "Comparison of Antigenic Sites of Subtype-specific Respiratory Syncytial Virus Attachment Proteins", J. Gen. Virol. 70:2953–2961, 1989.

Walsh et al., "Protection from Respiratory Syncytial Virus Infection in Cotton Rats by Passive Transfer of Monoclonal Antibodies", Infection and Immunity 43:756–758, 1984.

Wathen et al., "Vaccination of Cotton Rats with a Chimeric FG Glycoprotein of Human Respiratory Syncytial Virus Induces . . . ", The Journal of Infectious Diseases 163:477–482, 1991.

Watt et al., "Determinants of susceptibility to challenge and the antibody response of adult volunteers given experimental . . . ", Vaccine 8:231–236, 1990.

Wright et al., "Evaluation of a live, attenuated respiratory syncytial virus vaccine in infants", The Journal of Pediatrics 88:931–936, 1976.

Hemming et al., Topically Administered Immunoglobulin Reduces Respiratory Syncytial Virus Shedding in Owl Monkeys, Antimicrobial Agents and Chemotherapy 32:1269–1270, 1988.

Harris et al. Tibtech 11:42–44 1993.

Sevier et al. Clin Chem 27:1797–1806 1981.

Winner, III et al. Infection & Immunology 59:977–982 1991.

Weltzin et al. J. Cell Biology 108:1673–1685, 1989.

Taylor et al. J. General Virology 73:2217–2223 1992. Stott et al. Develop. Biol. Standard. Vol. 57:237–244, 1984.

Johnson et al. J. Cell Biochem Suppl 15E:120, 1991.

Downham et al. British Medical J. 2:274–276 1976.

Scott et al. J Medical Virol. 17:83–93, 1985.

Waldman, Science 252:1657–1602, 1991.

MONOCLONAL IGA ANTIBODY SPECIFIC FOR RESPIRATORY SYNCYTIAL VIRUS, A HYBRIDOMA CELL LINE THAT PRODUCES THIS ANTIBODY AMD METHODS OF USING THE ANTIBODY TO DIAGNOSE RSV INFECTION

This is a continuation of application Ser. No. 08/099,477, filed Jul. 30, 1993, now abandoned.

The present invention relates to antibodies directed against Respiratory Syncytial virus (RSV). More particularly, the present invention provides monoclonal IgA antibodies to RSV which are secreted by the hybridoma cell line HNK20. The antibody can be used for the prevention or treatment of RSV infection and disease, and the monoclonal antibodies may be employed in assay systems for RSV infection.

BACKGROUND OF THE INVENTION

RSV appears in predictable yearly outbreaks. Annual outbreaks of lower respiratory tract disease in young children have been noted since at least the early 1940's (1). RSV was implicated as the major cause of these outbreaks soon after its discovery in 1956 (2, 3). RSV infects adults as well as infants, and causes serious lower respiratory tract disease primarily in very young infants, children with pulmonary or cardiac disease, the immunologically compromised and the elderly (4). RSV infection is responsible for 40% to 50% of cases of children hospitalized with bronchiolitis and 25% of children with pneumonia (5). The number of cases requiring hospitalization in 1993 has been estimated at 91,000 with a cost of approximately $300,000,000 (5). Spread of the virus in hospitals is a particularly serious problem. When RSV infections are present in a hospital, 20% to 45% of infants may acquire a nosocomial RSV infection (6). Premature infants and those hospitalized for cardiac or pulmonary diseases are thus placed at acute risk of developing lower respiratory tract disease. In a study of children with congenital heart disease, 21% of RSV infections were acquired nosocomially (6).

To date, an effective vaccine against RSV has not been developed. In lieu of an active vaccine to protect high risk patients, especially infants, passive application of antibody may serve to protect these children during periods of known exposure. Intravenous treatment with immunoglobulin (IgG) containing anti-RSV activity is being tested in clinical trials (7, 8). While intravenous IgG might prevent lower respiratory tract disease, the evidence suggests that large doses and volumes of this material are required. Such treatment is not without potential adverse effects, including volume overload and circulatory failure.

In humans, upper airway infection generally precedes involvement of the lower respiratory tract (4). A study of modes of transmission shows that the virus is spread via fomites and self-inoculation of the nose or eyes rather than by aerosol, suggesting that the infection does not initiate in the lower respiratory tract (14). Viral infection is normally limited to the respiratory tract epithelium, and cell-to-cell spread is probably via secretions and cell-cell fusion (4). Fused cells can be recovered from lung aspirates of infected patients (4), but the importance of syncytium formation in pathogenesis or viral spread is not known.

None of the current approaches to prophylaxis of RSV focuses on the prevention of initial stages of infection in the upper respiratory tract. Natural immunity in this compartment of the respiratory tract is mediated by IgA antibodies in the nasal secretions.

The immune response to RSV infection is short-lived. This allows repeated infection to occur in adults and children. In an adult challenge study, 40% of the subject could be infected 3 times with the same challenge strain over a period of 26 months (15). Up to 75% of children infected during their first season of RSV exposure are reinfected in their second season (16), although severe disease was uncommon after the initial infection. Circulating anti-RSV antibody can be protective when present in sufficient quantity, but its importance has been difficult to resolve. In animals, human IgG or specific monoclonal antibodies administered parenterally can protect against replication of the virus in the lung (9, 17–19). High levels of circulating anti-RSV antibody protects primarily the lower respiratory tract (9). Moreover, the role of secretory antibody in protection against RSV has not been clearly established, but it appears that it may be an important mediator of the upper airway immunity. The titer of neutralizing antibody in nasal secretions correlates with decreased virus shedding and protection against disease in adult volunteers challenged with RSV (20, 21). A decrease in viral shedding also correlates with the appearance of anti-RSV secretory IgA (sIgA) in nasal secretions of infants (22). However, not all of the neutralizing activity of nasal secretions is due to antibody (22). A correlation between nasal anti-RSV antibody level and protection against infection or severe disease has not been demonstrated in human infants (15, 22–25), but in animals, mucosal immunization protects against nasal infection (26–27).

RSV is an enveloped, negative strand RNA virus belonging to the genus Pneumovirus of the Paramyxoviridae family (10, 11). Two glycoproteins, 90 kD and 68 kD, are exposed on the surface of the virion. The 90 kD heavily glycosylated G protein is responsible for binding of virus particles to target cells (12). The 68 kD F protein mediates fusion of the viral envelope with the cell membrane and syncytium formation (13). The F and G surface glycoproteins referred to above appear to be the primary protective antigens, with the nucleoprotein N and the envelope protein M2 having minor protective activity. Neutralizing and fusion-inhibiting monoclonal antibodies have been mapped to specific domains of F glycoprotein (9, 28–31). Monoclonal antibodies against the G glycoprotein are less likely to neutralize virus than those against the F glycoprotein and do not have fusion inhibiting activity (32–34). The amino acid sequence of F glycoprotein is approximately 90% conserved between the RSV subgroups responsible for human infection (35). Conserved epitopes include some that mediate neutralization and fusion inhibition (19, 35). The G glycoprotein which is primarily responsible for differences between subgroups A and B is only 53% conserved between the two subgroups (36). Immunization with the vaccinia virus recombinant expressing N or M2 induces a minor protective response in mice (37, 38). This response may be due primarily to CTL activity, since anti-N monoclonal antibody does not protect when passively administered to mice (39). Moreover, N has been shown to be a CTL target in mice and humans (37).

An early vaccine consisting of formalin-inactivated alum-adsorbed RSV elicited neutralizing and complement-fixing serum antibody in a clinical trial. However, vaccinated children were not protected and had more severe lower respiratory tract disease upon subsequent natural infection (40). The reason for the enhanced disease has not been fully explained. Cotton rats immunized with formalin-inactivated RSV developed a similar pathological response (41), providing a method of testing the safety of new vaccines.

Efforts have focused in the past on developing attenuated live virus vaccines. To date, those vaccines have been found to be ineffective (42), insufficiently attenuated (43, 44), or genetically unstable (45, 46). More recent efforts have focused on the RSV surface glycoproteins F and G. Immunization with purified F glycoprotein has been shown to be effective in cotton rats and is currently in clinical trials (47–48). However, some preparations of F glycoprotein have been shown to cause enhanced lung pathology upon subsequent RSV infection in cotton rats (49). Recombinant chimeric FG glycoprotein produced in a baculovirus expression system elicits a protective immune response in cotton rats when given parenterally (50). As with F glycoprotein alone, FG vaccine was also shown to cause some enhanced pulmonary pathology in cotton rats (51, 52). Vaccinia virus recombinants expressing F, G or M2 envelope protein, or the nucleoprotein N, have been tested in several animal models. F and G recombinants have shown the most promise, inducing protective immunity in mice (53, 54), cotton rats (55) and owl monkeys (56). The response in chimpanzees however was markedly lower (57). Adenovirus is also being examined as a vector for RSV F glycoprotein (58).

A need exists, therefore, for effective approaches to the prevention of RSV disease. The present invention seeks to fill that need.

SUMMARY OF THE INVENTION

According to one aspect, the present invention provides a neutralizing monoclonal IgA antibody to Respiratory Syncytial Virus (RSV), sometimes referred to hereinafter as HNK20, that is directed against the F glycoprotein of RSV, and is secreted by the hybridoma cell line HNK20. Preferably, the monoclonal antibodies are in substantially pure form free from other immunological material.

According to another aspect, the present invention provides a composition comprising one or more of the monoclonal IgA antibodies and a suitable carrier or diluent.

The invention further provides a method of treating or preventing Respiratory Syncytial Virus infection in a host, which comprises the step of administering to said host an amount of antibody secreted by hybridoma cell line HNK20 sufficient to achieve said treatment or prevention of disease. The antibody may be administered parenterally to the host, e.g. intravenously, or may be administered to a mucosal surface of the host. A particularly preferred mode of administration is intranasal.

The invention also provides pharmaceutical compositions suitable for treatment or prevention of Respiratory Syncytial Virus infection, comprising an effective amount of an antibody secreted by hybridoma cell line HNK20 and a pharamaceutically acceptable carrier or diluent.

The present invention also provides a process for producing monoclonal IgA antibodies to Respiratory Syncytial Virus, in which hybridoma cell line HNK20 is cultured, and the antibodies so produced are recovered. The process is preferably carried out by culturing the cell line in vitro in a nutrient culture medium therefore and recovering the antibodies from the culture supernatent.

The invention also provides a method of diagnosing the presence of respiratory syncytial virus antigen in a biological sample, in which the antigen is contacted with monoclonal IgA antibodies secreted by hybridoma cell line HNK20 and the presence of the antigen is detected by immunofluorescent microscopy or immuno-electron microscopy or in a solid-phase radiometric assay system or in an enzyme-linked immunoassay. The method is preferably carried out by incubating a sample taken from a human or animal with HNK20 antibody in solid phase, washing the solid phase and incubating it with radiolabeled or enzyme-labeled HNK20 antibody as tracer. The sample may be nasal secretions, nasal washings, pharyngeal secretions or bronchial secretions.

The invention further provides a method of isolating Respiratory Syncytial Virus antigen from a biological sample, which comprises contacting the sample with HNK20 antibody in the solid phase to cause Respiratory Syncytial Virus antigen to bind to the antibody, and subsequently separating the Respiratory Syncytial Virus antigen from the solid phase.

The invention yet further provides a kit comprising a first container containing a plastics substrate coated with HNK20 antibody and a second container containing antibodies secreted by hybridoma cell line HNK20 to which antibody a radio-label or enzyme label has been attached. Preferably, the plastics substrate is a polystyrene in the forms of beads, sticks or tubes.

According to a further aspect of the invention, there is provided the hybridoma cell line HNK20 which secretes monoclonal antibodies to RSV antigen. The cell line is preferably in substantially pure form free from other cellular material.

Compositions of the cell line are also provided according to the invention, comprising the cell line together with a nutrient medium capable of maintaining the cell line. An appropriate medium contains a source of carbon, a source of nitrogen and, if desired, vitamins and/or organic salts.

According to a yet further aspect of the invention, there is provided a process for propagating the hybridoma cell line HNK20 comprising culturing the cells in a nutrient culturing medium therefor. The method of propagation also represents a means of producing the antibodies of the invention which may be separated from the culture medium. Preferably, the propagation of the hybridoma cell line HNK20 is carried out in vitro, wherein the cell line is cultured in a nutrient culture medium therefor. An appropriate nutrient culture medium for the cells of the present invention contains a source of carbon, a source of nitrogen and if desired vitamins and/or inorganic salts. A suitable nutrient medium is RPMI 1640 medium supplemented with 10% fetal bovine serum. Another suitable nutrient medium is Sigma Serum-free and Protein-free Hybridoma medium.

An important advantage of the antibody of the invention is that it reduces infection of the upper airways, where IgA is the major effector antibody isotype. Particularly good results are obtained when the antibody is administered intranasally. This is one feature which distinguishes the antibody of the present invention from other monoclonal antibody or immune globulin preparations which are administered parentally (via intravenous or intramuscular routes) to reduce infection of the lower respiratory tract while allowing upper respiratory tract infection to occur. The monoclonal antibody of the present invention is particularly useful for passive treatment and protection of hospitalized patients, especially infants, from RSV while at the same time limiting viral spread during outbreaks.

As noted earlier, administration by the intranasal route is preferred over the parenteral route in that the intranasal route has the advantage of greater safety. Adverse reactions of the allergic type to topical (intranasal) antibody are localized to the nose or upper airways rather than being systemic hypersensitivity reactions, that can have severe consequences for the host. Parenteral administration of immunoglobulin (IVIG) or monoclonal antibodies may result in anti-idiotypic antibody responses with potential adverse effects upon the recipient. The concentration of intranasal antibody required for protection is significantly lower (200 times less) than that required for parenteral antibody. Small infants may not tolerate the large amounts (volumes) of IVIG required for protection. Finally, IgA applied topically may have advantages over IgG in being polyvalent rather than monovalent, and hence more efficacious in binding or neutralizing virus. Moreover, IgA binds complement to a very limited degree as compared to IgG, with the result that IgA is less likely to participate in inflammatory reactions that could cause side effects in the treated individual.

BRIEF DESCRIPTION OF THE DRAWINGS

The invention will now be further described with reference to the accompanying drawings, in which.

DETAILED DESCRIPTION OF THE INVENTION

Hybridoma cell lines were prepared by immunizing BALB/c mice with live RSV delivered intranasally or intragastrically. Mucosal immunization was effected to preferentially elicit a mucosal IgA response. Four days after the final immunization, the mice were sacrificed and lung and Peyer's patch leukocytes were isolated and separately fused with P3U1 myeloma cells. The resulting hybridomas were screened for anti-RSV antibody production by ELISA. Lung cell fusions yielded 24 hybridomas secreting anti-RSV antibody. The fusions were carried out according to the methods of Kohler and Milstein (59). Eight of these antibodies were IgA's. No anti-RSV hybridomas were obtained from Peyer's patch fusion.

After their identification and cloning, anti-RSV monoclonal antibodies were tested for recognition of RSV subgroups A and B. Binding to RSV subgroup A (strains A2 and Long) and subgroup B (strain 18537) was compared by ELISA. The results are set forth in Table 1 below.

TABLE 1

Binding of mAbs to RSV strains A2 (subgroup A), Long (subgroup A) and 18537 (subgroup B)

| mAb | $OD_{405}$ | | |
|---|---|---|---|
| | A2 (A) | Long (A) | 18357 (B) |
| Experiment R0265A | | | |
| HNK 4 | 0.214 | 0.162 | 0.009 |
| HNK 10 | 0.054 | 0.044 | 0.053 |
| HNK 11 | 0.141 | 0.123 | 0.146 |
| HNK 12 | 0.031 | 0.021 | 0.056 |
| HNK 13 | 0.026 | 0.004 | 0.009 |
| HNK 16 | 0.540 | 0.598 | 0.579 |
| HNK 17 | 0.176 | 0.176 | 0.066 |
| HNK 18 | 0.356 | 0.423 | 0.374 |
| HNK 19 | 0.151 | 0.204 | 0.137 |
| Experiment R0298A | | | |
| HNK 20 | 0.191 | 0.227 | 0.146 |
| HNK 21 | 0.250 | 0.295 | 0.248 |
| HNK 22 | 0.122 | 0.205 | 0.062 |
| HNK 23 | 0.081 | 0.186 | 0.026 |
| HNK 24 | 0.230 | 0.258 | 0.203 |

Figure 1:
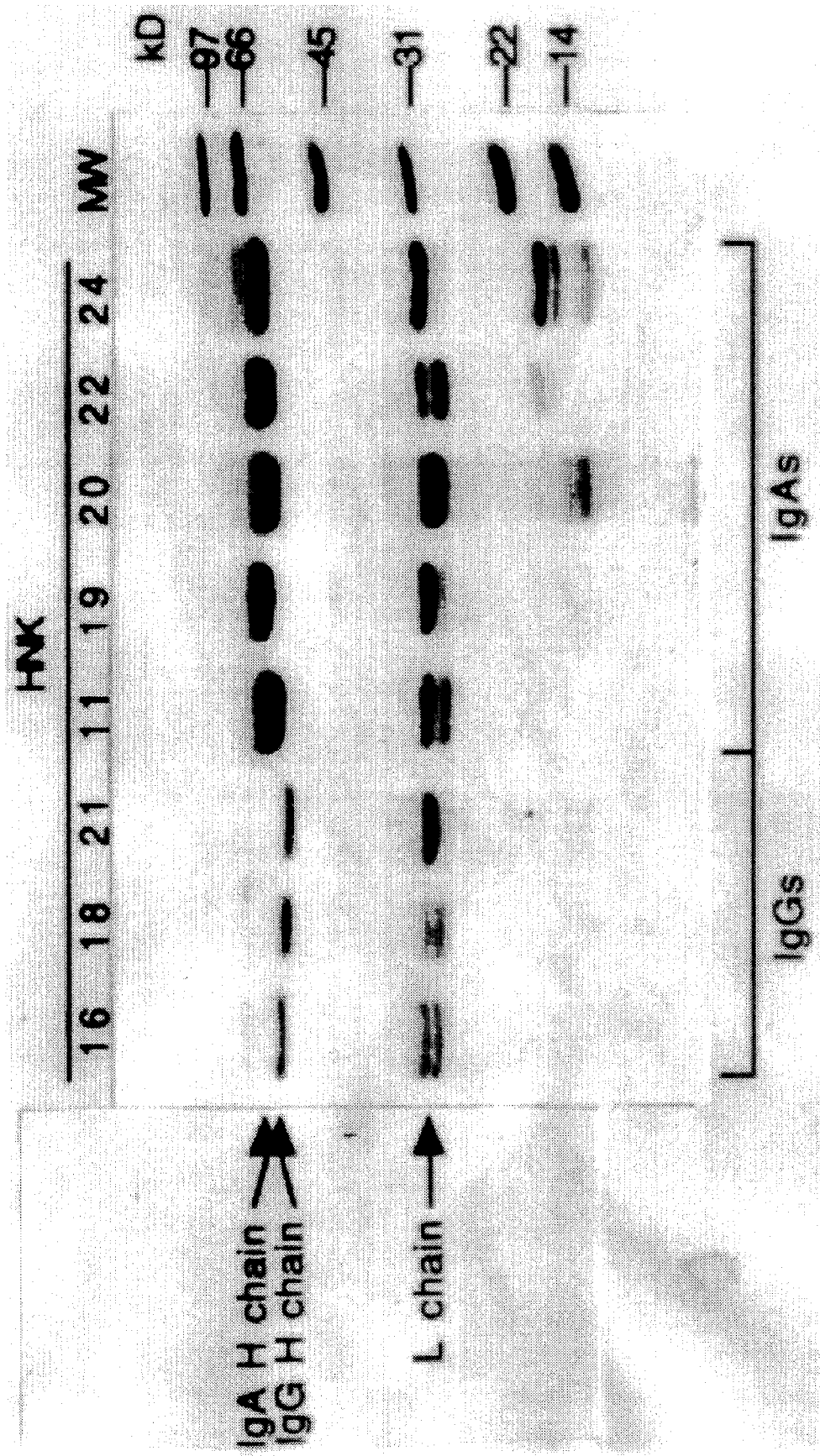
FIG. 1 shows a PAGE analysis of anti-RSV HNK monoclonal antibodies grown in protein-free medium.

Five of eight IgAs (HNK 11, 19, 20, 22 and 24) were found to bind to all three strains. These five monoclonal antibodies, along with three subgroup cross-reactive $IgG_{2a}$ monoclonal antibodies (HNK 16, 18 and 21) were selected for further study. The eight cross-reactive hybridomas were adapted to growth in protein-free culture medium. The culture medium was collected, concentrated and assayed for antibody concentration. FIG. 1 shows each concentrated antibody preparation run out on an acrylamide gel and stained with Coomassie blue.

The above anti-RSV monoclonal antibodies were tested for in vitro neutralization by a plaque-reduction assay using strain A2 (see Table 2). Two antibodies, HNK20 and HNK24, showed neutralizing activity. HNK20, the antibody of the present invention, was the most effective giving a 50% reduction in plaque numbers at a concentration of 0.1 µg/ml or less. The 50% effective dose of HNK20 was the same for neutralization of 18537, a subgroup B strain.

TABLE 2

| In vitro neutralization of RSV | | |
|---|---|---|
| MAb | Isotype | Neutralization[a] |
| HNK11 | IgA | >100 µg/ml |
| HNK19 | IgA | >100 µg/ml |
| HNK20 | IgA | 0.1 µg/ml |
| HNK22 | IgA | >100 µg/ml |
| HNK24 | IgA | 10 µg/ml |
| HNK16 | IgG2a | >100 µg/ml |
| HNK18 | IgG2a | >100 µg/ml |
| HNK21 | IgG2a | >100 µg/ml |

[a]lowest antibody concentration giving 50% plaque reduction.

It will be seen from Table 2 that none of the IgG monoclonal antibodies neutralizes virus.

The above-described eight anti-RSV monoclonal antibodies have been screened for protection against pulmonary RSV infection in the mouse model. Mice were challenged intranasally with approximately $10^6$ PFU of virus 24 hours after an intranasal dose of anti-RSV or nonspecific control (2D6—an IgA against *Vibrio cholerae*) monoclonal antibody. Four days later, the lungs were removed and homogenized and the virus content of lung tissue determined. The results are set forth in Table 3.

TABLE 3

In vivo protection experiments: Reduction in lung virus titer after intranasal treatment with monoclonal antibody 24 h before RSV challenge.

| Experiment number | Treatment | Lung PFU/g (×10⁵) |
|---|---|---|
| 1 | 2D6 | 1.8 ± 0.1 |
|   | HNK16 (IgG) | 1.4 ± 0.4 |
|   | HNK18 (IgG) | 0.3 ± 0.1 |
|   | HNK21 (IgG) | 0.7 ± 0.1 |
| 2 | 2D6 | 0.9 ± 0.2 |
|   | HNK11 (IgA) | 1.0 ± 0.3 |
|   | HNK19 (IgA) | 0.6 ± 0.2 |
|   | HNK22 (IgA) | 0.7 ± 0.2 |
| 3 | 2D6 | 1.1 ± 0.3 |
|   | HNK20 (IgA) | 0.02 ± 0.02 |
| 4 | 2D6 | 0.7 ± 0.4 |
|   | HNK24 (IgA) | 0.3 ± 0.1 |

Treatment with monoclonal antibodies HNK18 (an IgG antibody) and HNK20 (the IgA antibody of the present invention) resulted in the reduction in lung viral titer of approximately 1 log or greater.

Figure 2:
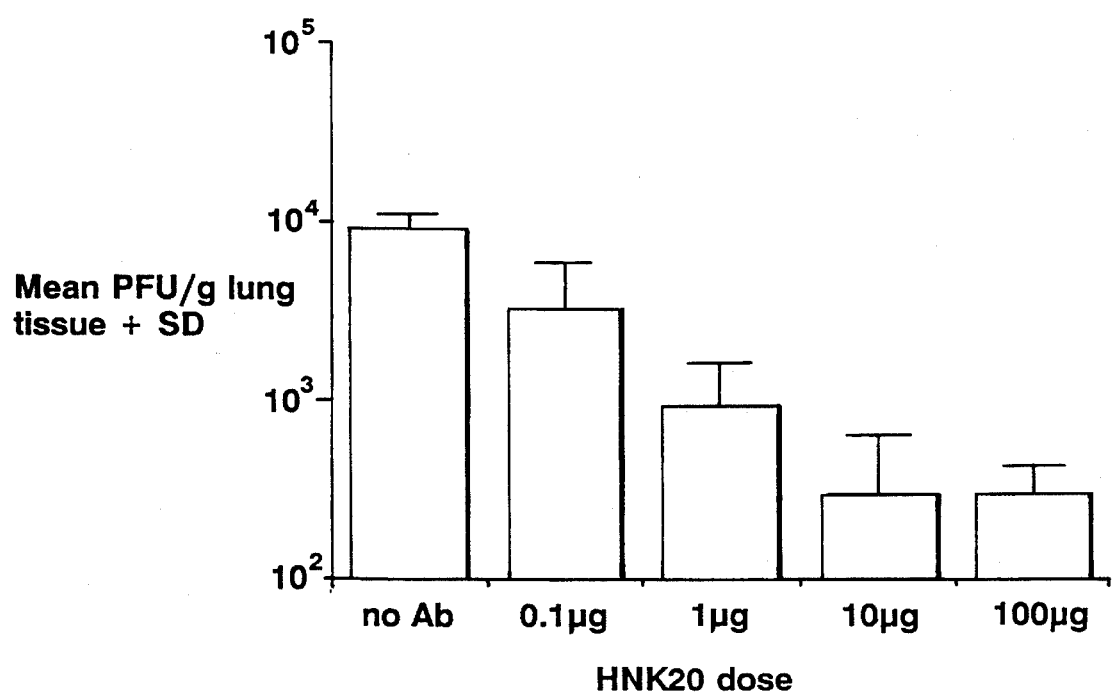
FIG. 2 shows the effect of increasing doses of HNK20 given intranasally to mice 1 hour prior to RSV challenge (significance by unpaired t-test; 0.1 µg, p=0.03; 1 µg, p=0.001; 10 µg, p=0.001; 100 µg, p=0.001)

The antibody HNK20 has been tested over a range of concentrations for its ability to protect against infection of mouse lungs. The results are set forth in FIG. 2. HNK20 antibody was given intranasally 1 hour prior to viral challenge. Maximum protection was seen at a dose of between 1 and 10 μg per mouse.

Figure 3:
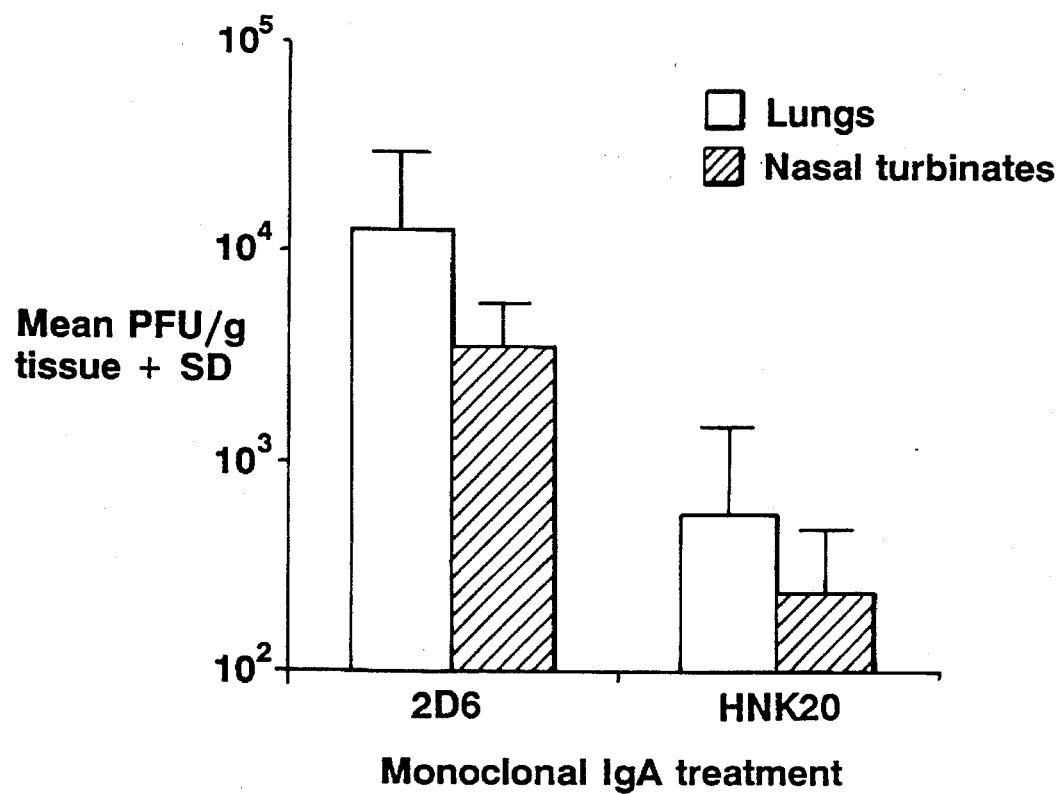
FIG. 3 shows intranasal treatment of mice with monoclonal IgA (HNK20 and 2D6) 1 hour prior to RSV challenge (significance by unpaired t-test: lungs, p=0.02; nasal turbinates, p=0.01)

The HNK20 monoclonal antibody of the present invention is able to protect against replication of RSV in nasal mucosa. This is demonstrated by the data set forth in FIG. 3. Mice were challenged as described above and PFU/g nasal turbinate tissue was determined four days after challenge. HNK20 or 2D6 monoclonal IgA was given 1 hour before viral challenge. HNK20 produced a greater than 1 log decrease in viral PFU in nasal tissue.

Figure 4:
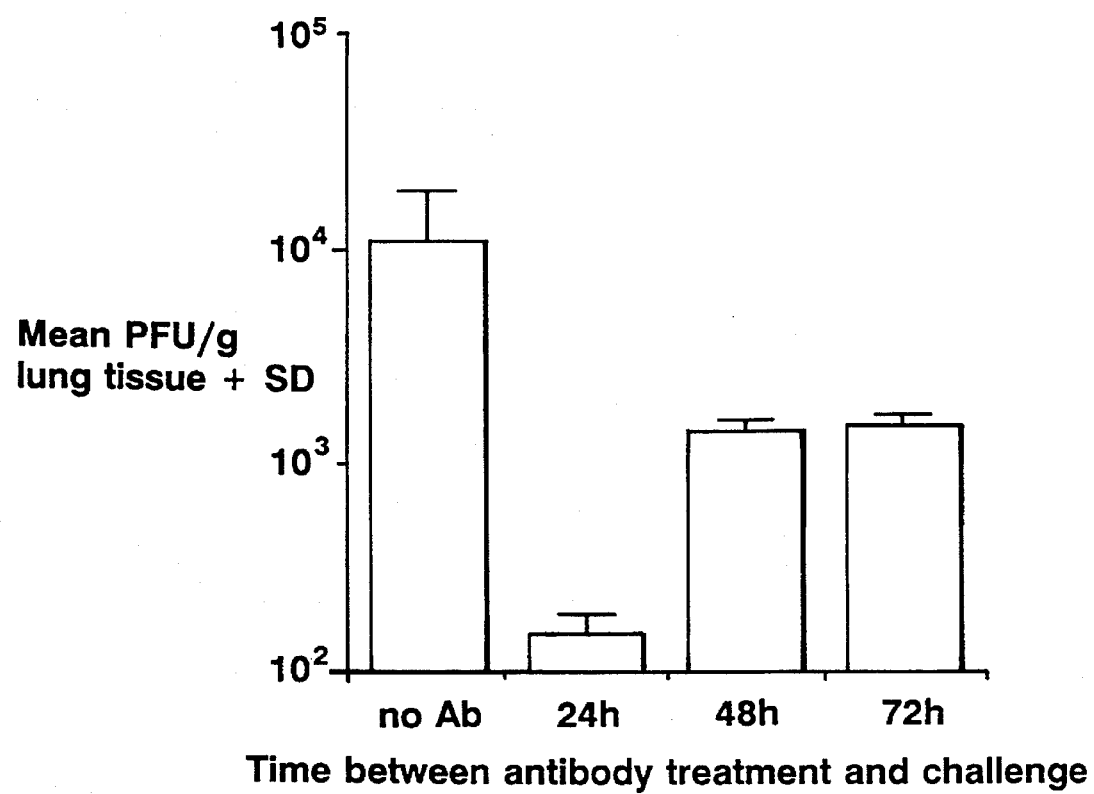
FIG. 4 shows intranasal treatment of mice with HNK20 1 to 3 days prior to RSV challenge (significance by unpaired t-test: 24 h, p=0.02; 48 h, p=0.03; 72 h, p=0.03)

Protection of the lungs of mice from infection was similar, whether HNK20 antibody was given 1 hour or 24 hours before viral challenge. FIG. 4 shows the effect on lung protection in mice when HNK20 is administered intranasally 24, 48 and 72 hours prior to challenge. Protection is seen at all three time points, with the mice treated 24 hours before challenge being better protected than those treated at 48 and 72 hours.

HNK20 was also tested for protective activity in cotton rats, a well established model for RSV infection of the respiratory tract. These studies were carried out by the Antiviral Research Branch of the National Institute of Allergy and Infectious Disease as part of their program for screening agents with antiviral activity. The experiments were conducted in the laboratory of Dr. Philip Wyde at the Baylor College of Medicine. HNK20 was administered intranasally 1 hour, 3 hours, and 6 hours prior to RSV challenge. Cotton rats were sacrificed 4 days after infection and titers of RSV in the lung homogenates and nasal washes assessed. Significant protection of both lung and nasal tissue was observed at all three time points (see Table 4). Many of the HNK20-treated cotton rats, particularly at the 1 hour time point, had no recoverable virus.

TABLE 4

1. Nasal wash titers on day +4

| Group | Treatment (mg/kg) | Individual RSV titers (log 10/0.05 ml) | | | | Mean | S.D. | No. infec. No./grp |
|---|---|---|---|---|---|---|---|---|
| | | 1 | 2 | 3 | 4 | | | |
| 1 | Placebo | 2.8 | 3.3 | 2.8 | 3.3 | 3.05 | 0.29 | 4/4 |
| 2 | HuISG | 0 | 0 | 0 | 0 | 0.00 | 0.00 | 0/4 |
| 3 | IgA-1 h | 0 | 0 | 0 | 0 | 0.00 | 0.00 | 0/4 |
| 4 | IgA-3 h | 0 | 0 | 0 | 1.6 | 0.45 | 0.90 | 1/4 |
| 5 | iGA-6 h | 1.8 | 1.8 | 0 | 0 | 0.90 | 1.04 | 2/4 |

0 = undetected (less than the minimal detectable titer [<1.3 log 10/0.5 ml])
HuISG = human immune serum globulin (Armour Pharmaceuticals)
IgA = OraVax IgA monoclonal antibody (Mab)

1. RSV titers in the lung on day +4

| Group | Treatment (mg/kg) | Individual RSV titers (log 10/g lung) | | | | Mean | S.D. | No. infec. No./grp |
|---|---|---|---|---|---|---|---|---|
| | | 1 | 2 | 3 | 4 | | | |
| 1 | Placebo | 3.3 | 2.8 | 2.8 | 2.8 | 2.93 | 0.25 | 4/4 |
| 2 | HuISG | 0 | 0 | 2.3 | 0 | 0.58 | 1.15 | 1/4 |
| 3 | IgA-1 h | 0 | 2.3 | 0 | 0 | 0.58 | 1.15 | 1/4 |
| 4 | IgA-3 h | 2.6 | 0 | 2.3 | 0 | 1.28 | 1.49 | 2/4 |
| 5 | IgA-6 h | 0 | 2.3 | 0 | 3.3 | 1.40 | 1.67 | 2/4 |

0 = undetected (less than the minimal detectable titer [<1.3 log 10/g lung])
HuISG = human immune serum globulin (Armour Pharmaceuticals)
IgA = OraVax IgA monoclonal antibody (Mab)

Figure 5:
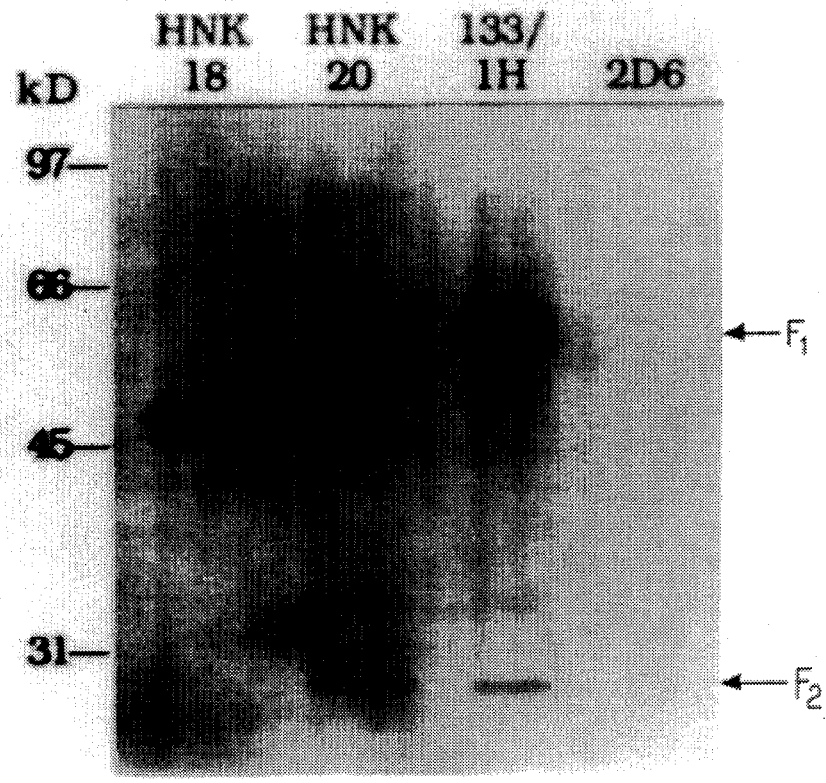
FIG. 5 illustrates immunoprecipitation of $^{35}$S-labelled RSV-infected lysate by monoclonal antibodies generated from cell lines HNK18, HNK20, 133/1H (anti-F), and 2D6 (anti-*V. cholerae*)

The protein specificities of HNK18 and HNK20 have been examined by immunoprecipitation of radiolabeled lysates of RSV-infected VERO cells. HNK20 precipitated a pair of proteins corresponding in mobility to the $F_1$ and $F_2$ subunits of the F glycoprotein. This is shown in FIG. 5. These bands co-migrated with the bands precipitated by 133/1H, a monoclonal antibody previously shown to bind to F glycoprotein. HNK18 precipitated a protein with a molecular weight of approximately 47 kD. The identity of this band has not yet been determined, but its molecular weight is close to that of N protein, which has a molecular weight of 43.5 kD. Further evidence for F glycoprotein specificity of HNK20 was provided by an ELISA in which the monoclonal antibody was shown to bind to VERO cells infected with a vaccinia virus recombinant expressing RSV F glycoprotein. This is shown in Table 5. Binding to uninfected VERO or VERO infected with glycoprotein G or hepatitis VP59 recombinants was negligible.

TABLE 5

Binding of mAbs to VERO infected with vaccinia recombinants expressing RSV F, RSV G, or hepatitis VP 59

| mAb | $OD_{405}$ | | | |
| --- | --- | --- | --- | --- |
| | uninfected | vac/VP59 | vac/F | vac/G |
| HNK20 | 0.011 | 0.000 | 0.137 | 0.003 |
| 133/1H (anti-F)* | 0.189 | 0.174 | 0.453 | 0.218 |
| 131/2G (anti-G)* | 0.191 | 0.176 | 0.193 | 0.317 |

*monoclonal antibodies against RSV (obtained from Biodesign International)

Figure 6:
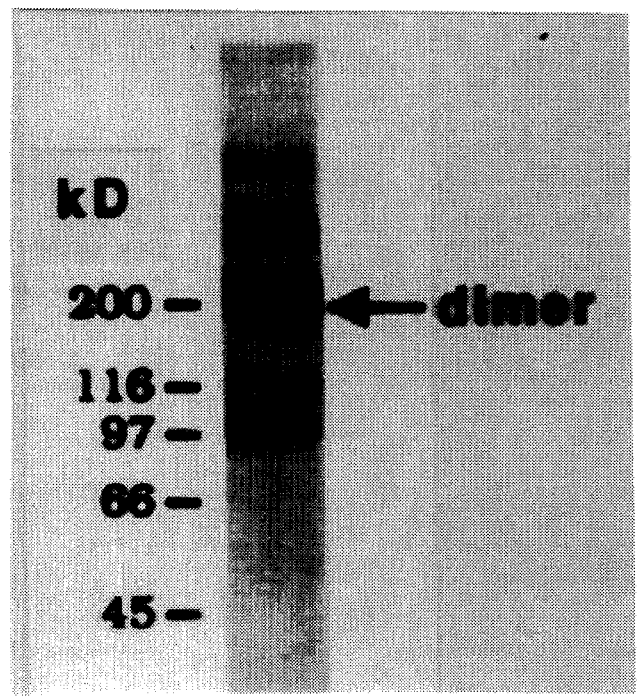
FIG. 6 shows an immunoblot of HNK20 IgA run on a non-reducing 5–15% gradient polyacrylamide SDS gel (gel was blotted to nitrocellulose and reacted with alkaline phosphatase-labelled rabbit anti-mouse IgA-alpha chain specific).

Structurally, HNK20 has been shown to possess k light chains by ELISA using light chain-specific antibodies. The polymeric structure of HNK20 was examined by running the monoclonal antibody on a 5 to 15% gradient acrylamide gel under non-reducing conditions and staining for IgA bands in an immunoblot. This is shown in FIG. 6. The antibody is shown to be produced in monomeric, dimeric and higher polymeric forms. The major species was dimeric.

Studies have shown that HNK20 antibody exhibits good storage properties under varying conditions. Thus, HNK20 antibody stored under various conditions for 1 to 2 months was examined by RSV-binding ELISA and gel electrophoresis under reducing and non-reducing conditions. The antibody proved to be very stable when stored at 4° C., −80° C., or −20° C. in glycerol. A slight reduction in ELISA reactivity and the appearance of lower molecular weight bands was found in the −80° C. and −20° C. samples at a two-month time point.

The cell line HNK20 secreting monoclonal antibody HNK20 mAb has been deposited with The American Type Culture Collection, situated at 12301 Parklawn Drive, Rockville, Md. 20852, USA, on Jul. 1, 1993, and has been accorded the accession number ATCC HB 11394.

The monoclonal antibody HNK20 secreted by the hybridoma of the invention may be recovered from mouse ascites fluid. This process of both propagating the cell lines and producing the antibodies represents a further aspect of this invention. These means of obtaining the monoclonal antibodies of the invention offers the advantage that the yield may, for example, be as much as 10-fold higher than the yield obtained from the bulk culture of the cells. The period of time normally taken to grow up in the mice is about 2 to 3 weeks.

The monoclonal antibody HNK20 secreted by the hybridoma of the invention may be also produced at high concentration and purity by culture of the hybridoma cells in a hollow fiber bioreactor such as the Maximizer 1000 produced by Endotronics, Inc. This means of obtaining the monoclonal antibodies of the invention offers the advantages of high yield (approximately 1 mg/ml) and greater purity than antibodies produced in mouse ascites.

The antibodies of the invention may be used unpurified from such sources as described above. Preferably, the antibodies are subjected to purification before use. For example, IgA monoclonal antibodies may be purified from cell culture fluid by sequential anion exchange chromatography on Q Sepharose followed by gel filtration using Sephacryl S-300, as described previously (60).

The monoclonal antibodies produced by the cell line HNK20 have particular utility in passive treatment of patients suffering or exposed to RSV. It is known that natural hosts for RSV infection are humans, chimpanzees and cattle. Non-human primates including cebus and owl monkeys develop clinical disease when infected with RSV. Moreover, RSV replicates in the upper respiratory tract of adult ferrets and replication also occurs in the lungs of lambs. The vast majority of recent studies have used cotton rats or mice as models to study RSV pathogenesis and protection against infection. RSV replicates in the upper and lower respiratory tracts of these species, with peak viral titers appearing after 4 or 5 days. These rodents are particularly suitable for immunological studies aimed at demonstrating protection against RSV. Studies of passive immunization with IgG have shown that the results obtained from rodents are predictive of the activity of IgG in monkeys and humans. The results obtained in mouse and cotton rat models for the present IgA monoclonal antibody are therefore believed to be predictive of probable efficacy in humans, including human infants.

The monoclonal antibodies can be used, according to one aspect of the invention, for the passive treatment or prevention of Respiratory Syncytial Virus infection in a host, including humans. The method comprises administering to the patient an effective amount of HNK20. Typically, the antibody is administered to a mucosal surface, and may be administered orally or intranasally. The amount of antibody which is administered will vary from 50 µg/kg to 5 mg/kg body weight.

For therapeutic and/or preventative use, the antibody compositions of the invention may be in solid or liquid form with a suitable pharmaceutical carrier and/or diluent known in the art. The compositions are prepared in a conventional manner and comprise an effective amount of the antibody, typically 50 µg/kg to 50 mg/kg body weight.

The compositions may be in the form of an injectable solution or in the form of solutions, suspensions or powder. Preferably, the composition is formulated for nasal delivery to provide protection of the upper respiratory tract or for aerosol delivery to provide protection of the lower respiratory tract.

The antibodies produced by cell line HNK20 also have utility in providing accurate screening tests for patients infected by RSV. The antibodies can be used in assay systems, employing for example immunofluorescent microscopy, or immuno-electron microscopy in detecting the presence of RSV in cellular material or in secretions. Quantitative assays may be carried out by solid phase radiometric assay.

A method of diagnosing the presence of respiratory syncytial virus antigen in a biological sample according to the invention includes contacting an antigen with monoclonal IgA antibodies secreted by hybridoma cell line HNK20 and detecting the presence of the antigen by immunofluorescent microscopy or immuno-electron microscopy or in a solid-phase radiometric assay system or in an enzyme-linked immunoassay. Preferably, a sample taken from a human or animal is incubated with HNK20 antibody in solid phase, followed by washing and incubating with radiolabeled or enzyme-labeled HNK20 antibody as tracer. In the assay system, the solid phase preferably comprises a plastic or glass substrate on which the antibodies are coated. The substrate is particularly preferred in the form of beads, sticks, tubes or plates, for example polystyrene.

The present invention also provides these coated substrates, e.g. beads, in a diagnostic kit. The kit comprises a first container which contains a plastics or glass substrate such as beads, sticks, plates or tubes coated with HNK20 antibodies and the second container containing HNK20 antibody to which a radiolabel has been attached.

Instead of employing a radiolabel, it is possible, as an alternative assay method in accordance with the invention, to employ for example an enzyme-label or a biotin-label which will generally be linked to the HNK20 antibody. Diagnosis of RSV infection is achieved by reacting a clinical specimen (containing RSV) with the substrate coated with HNK20 antibodies. After a suitable incubation period, the second (radio- or enzyme-labeled) HNK20 antibody is added (followed by substrate in the case of enzyme-labeled HNK20). The reaction measures the presence and amount of RSV antigen in the clinical sample.

The monoclonal antibodies of the present invention when coupled to a solid phase such as bromide activated Sepharose can also be used to remove RSV from human or animal material either for the purpose of preparing RSV in a purified form for use in preparing vaccines or for the removal of RSV from material to be given to patients. The present invention therefore provides a method of isolating RSV antigen from a biological sample comprising contacting the biological sample with HNK20 antibodies in the solid phase to cause binding to the antigen to the antibody and subsequently separating the desired purified material from the solid phase.

The HNK20 hybridoma can be used to construct novel antibodies comprising mouse and human sequences. IgA heavy and light chain variable domains from HNK20 are combined, through recombinant DNA techniques, with human immunoglobulin heavy and light chain constant domains, to yield antibodies with predominantly human sequence and the binding specificity of HNK20. Such antibodies, termed chimeric or humanized antibodies, are particularly useful for parenteral treatment of humans as they are less likely to provoke an immune or allergic response to the antibody.

HNK20 monoclonal IgA antibodies can be bound to secretory component to yield complexes with increased resistance to digestion by proteolytic enzymes. Secretory component is combined with polymeric IgA in one of several ways. In one method, IgA antibodies and secretory component are mixed in solution and allowed to associate. In another method, the IgA-secreting hybridoma cells are transfected with an expression vector containing the cDNA for secretory component. The resulting cells produce IgA-secretory component complexes. In a third method, a cultured epithelial cell line, such as MDCK cells, is transfected with an expression vector containing the cDNA for polymeric immunoglobulin receptor. Transfected epithelial cells are grown on porous membrane filters in chambers in which the medium bathing the apical and basolateral sides of the cells are separate. Polymeric immunoglobulin receptors effect transport of IgA from the basolateral medium to the apical medium. Polymeric IgA is added to the basolateral medium and IgA is released into the apical medium in association with secretory component, a cleaved portion of the polymeric immunoglobulin receptor.

EXAMPLES

The invention will now be further illustrated by the following non-limiting examples.

Example 1

Three mice infected by being given $10^6$ PFU virus in a volume of 25 µl intranasally while under isoflurane anesthesia. After 4 days nasal turbinates are removed and a pooled 10% homogenate of nasal tissue in tissue culture medium is prepared. The sample is titrated by plaque assay, diluted to $10^6$ PFU/25 µl and inoculated into another group of 3 mice. Continued passages are performed. After adaptation to mice, a significant increase in lung virus titers is observed. The virus levels are tested at days 3, 4, 5, and 6 after inoculation to determine the peak of viral replication. The optimal conditions defined by these experiments are used for all subsequent mouse challenge experiments.

Example 2

The amount of HNK20 required for protection is tested by applying different amounts of monoclonal antibody intranasally 1 or more hours before viral challenge. Amounts ranging from 0.1 to 100 µg per mouse are given intranasally in a volume of 25 µl while mice are under isoflurane anesthesia.

To carry out animal experiments, approximately 50 mg of monoclonal IgA antibody is produced. The antibodies are partially purified and processed to yield monomeric and polymeric fractions of HNK20. Hybridoma HNK20 is cloned 3 times and adapted to growth in protein-free medium (Sigma Chemical Company). The hybridoma is grown in four 500 ml spinner flask allowing 2L of spent medium to be collected every 2 days. A total of 8L is collected. The medium is concentrated approximately 200 fold in a stirred cell with a 100 kD cut-off membrane. The resulting crude concentrate contains about 50% pure monoclonal antibody at about 2–5 mg/ml.

HNK20 monoclonal antibody IgA is passed over a DEAE-sepharose column and eluted with 0.3M sodium chloride. This material is greater than 90% IgA, and is separated into monomeric, polymeric and aggregate fractions by Sephacryl S300 size exclusion chromatography. Molecular weight determinations are made by FPLC analysis and SDS-PAGE using a 5 to 15% gradient gel.

Example 3

The length of protection afforded by HNK20 monoclonal IgA is examined when the antibody is delivered to a viscous or bioadhesive carrier. Carriers to be tested include methylcellulose and neutralized polyacrylic acid. A solution of 50 µg/ml HNK20 in 0.25% methylcellulose or 50 µg/ml HNK20 in 1.5% polyacrylic acid is prepared. Mice are treated by intranasal instillation of 10 µl of antibody-carrier mixture. Control mice receive non-specific monoclonal IgA 2D6 in saline, 2D6 mixed with carriers, or HNK20 in saline. Different groups of mice are challenged intranasally with RSV at 1 hour, 5 hours, 10 hours or 15 hours after treatment. Four days after challenge, mice are sacrificed and RSV titers in nasal tissues are are determined. Carriers that extend the length of protection are examined further for effects on dose required for protection and adverse effects.

REFERENCES

1. Adams, J M. 1941. J. Pediatr. 20:405–420.
2. Morris, J A., B. R. E., and R E Savage, 1956. Proc. Soc. Exp. Biol. Med. 92:544–549.
3. Chanock, R M, B. Roizman and R Myers. 1957. Am. J. Hyg. 66:281–290.
4. McIntosh, K and R M Chanock. 1990. in Virology, B N Fields and D M Knipe. eds. 1990. Raven Press, New York, p. 1045–1074.
5. Heilman, C A. 1990. J. Infect. Dis. 161:402–6.

6. Graman, P S and C B Hall. 1989 Infect. Dis. Clin. N. Amer. 3:815.
7. Hemming, V G, W Rodriguez, H W Kim, C D Brandt, et al 1987. Antimicrob Agents Chemother 31:1882–6.
8. Groothuis, J R, M J Levin, W. Rodgriguez, C B Hall, C E Long, H W Kim, B A Lauer and V G Hemming. 1991. Antimicrob Agent Chemother 35:1469–73.
9. Walsh, E E, J J Schlesinger and M W Brandriss. 1984. Infect. Immun. 43:756–758.
10. Fenner, F. 1975. Virology 71:371–378.
11. Huang, Y T and G W Wertz. 1982. J. Virol. 43:
12. Walsh, E E, J J Schlesinger and M W Brandreiss. 1984. J Gen Virol 65:761–767.
13. Walsh, E E, M W Brandreiss and J J Schlesinger. 1985. J Gen Virol 66:409–415.
14. Hall, C B and R G J Douglas. 1981. J Pediatr 99:100–3.
15. Hall, C B, E E Walsh, C E Long and K C Schnabel. 1991. J Infect Dis 163:693–698.
16. Glezen, W P, L H Taber, A L Frank and J A Kasel. 1986. Am J Dis Child 140:543–546.
17. Taylor, G., E J Stott, M Brew, B F Fernie, P J Cote, A P Collins, M Hughes and J Jebbett. 1984. Immunology 52:137–42.
18. Prince, G A, V G Hemming and R M Chanock. 1986. Pediatr Infec Dis 5:S201–S203.
19. Tempest, P R, P Bremmer, M Lambert, G Taylor, J M Furze, F J Carr and W J Harris. 1991. Biotechnology 9:266–271.
20. Mills, J5, K J E Van, P F Wright and R M Chanock. 1971. J Immunol 107:123–30.
21. Watt, P J, B S Robinson, C R Pringle and D A Tyrell. 1990. Vaccine 8:231–6.
22. McIntosh, K. H B Masters, I Orr, R K Chao and R M Barkin. 1978. J Infect Dis 138:24–32.
23. Scott, R and P S Gardner. 1970. J Hyg (Camb) 68:581–588.
24. Bruhn, R W and A S Yeager. 1977. Am J Dis Child 131:145–8.
25. Kaul, T N, R C Welliver, D T Wong, R A Udwadia, R N Riddlesberger and P L Ogra. 1981. Am J Dis Child 135:1013–1016.
26. Reuman, P D, S P Keely and G M Schiff. 1990. J Med Virol 32:67–72.
27. Kanesaki, T, B R Murphy, P L Collins and P L Ogra. 1991. J Virol 65:657–63.
28. Trudel, M, F Nadon, C Seguin, G Dione and M Lacroix. 1987. J Gen Virol 68:2273–80.
29. Beeler, J A and K van Wyke Coelingh. 1989. V Virol 63:2941–50.
30. Lopez, J A, C Penas, B B Garcia, J A Melero and A Portela. 1990. J Virol 64:927–30.
31. Paradiso, P R, B T Hu, R Arumugham and S Hildreth. 1991. Vaccine 9:231–7.
32. Norrby, E, M A Mufson, H Alexander, R A Houghten and R A Lerner. 1987. Proc Natl Acad Sci USA 84:6572–6576.
33. Garcia-Barreno, B, C Palomo, C Penas, T Delgado, P Perez-Brena and J A Melero. 1989. J Virol 63:925–932.
34. Walsh E E, C B Hall, J J Schlesinger, M W Brandriss, S Hildreth and P Paradiso. 1989. J Gen Virol 70:2953–2961.
35. Toms, G L. 1991. FEMS Microbiol Immunol 76:243–256.
36. Johnson, P R, M K Spriggs, R A Olmsted and P L Collins. 1987. Proc Natl Acad Sci USA 84:5625–5629.
37. King, A M Q, E J Stott, S J Langer, K K-Y Yound, L A Ball and G W Wertz. 1987. J Virol 61:2885–2890.
38. Connors, M, P L Collins, C Y Firestone and B R Murphy. 1991. J Virol 65:1634–7.
39. Taylor, G E J Stott, M Brew, F. B. G., P C Cote, A P Collins, M Hughes and J Jebbett. 1984. Immunology 52:137–142.
40. Kapikian, A Z, R H Mitchell, R M Chanock, R A Shvedoff and C E Stewart. 1969. Am J Epidemiol 89:405–421.
41. Prince, G A, A B Jenson, V G Hemming, B R Murphy, E E Walsh, R L Horswood and R M Chanock. 1986. J Virol 57:721–728.
42. Belshe, R B, L P Van Loris and M A Mufson. 1982. J Infect Dis 145:311–319.
43. Wright, P F, T Shinovaki, W Fleet, S H Sell, J Thompson and D T Karzon. 1976. J Pediatr 88:931–939.
44. Kim, H W, J O Arrobio, C D Brandt and et al. 1973. Pediatrics 52:56–63.
45. McIntosh, K, A M Arbeter, M K Stahl, I A Orr, D S Hodes and E F Ellis. 1974. Pediatr Res 8:689–696.
46. Hodes, D S, H W Kim, R H Parrott, E Camargo and R M Chanock. 1974. Proc Sco Exp Biol Med 145:1158–1164.
47. Walsh E E, C B Hall, M Briselli, M W Brandriss and J J Schlesinger. 1987. J Infec Dis 155:1198–1204.
48. Routledge, E G, M M Willcocks, A C R Samson, L Morgan, R Scott, J J Anderson and G L Toms. 1988. J Gen Virol 69:293–303.
49. Murphy, B R, A V Sotnikov, L A Lawrence, S M Banks and G A Prince. 1990. Vaccine 8:497–502.
50. Brideau, R J, R R Walters, M A Stier and M W Wathen. 1989. J Virol 70:26637–44.
51. Wathen, M W, T J Kakuk, R J Brideau, E C Hausknecht, S L Cole and R M Zaya. 1991. J Infect Dis 163:477–82.
52. Connors, M, P L Collins, C Y Firestone, A V Sotnikov, A Waitze, A R Davis, P P Hung, R M Chanock and B R Murphy. 1992. Vaccine 10:475–484.
53. Stott, E J, L A Ball, K K Young, J Furze and G W Wertz. 1986. J Virol 60:607–613.
54. Olmsted, R A, N Elango, G A Prince, B R Murphy, P R Johnson, B Moss, R M Chanock and P L Collins. 1986. Proc Natl Acad Sci USA 83:7462–7466.
55. Elango, N, G A Prince, B R Murphy, S Venkatesan, R M Chanock and B Moss. 1986. Proc Natl Acad Sci USA 83:1906–1910.
56. Olmsted, R A, R M L Buller, P L Collins, W T London, J A Beeler, G A Prince, R M Chanock and B R Murphy. 1988. Vaccine 6:519–524.
57. Collins, P L, R H Purcell, Wt London, L A Lawrence, R M Chanock and B R Murphy. 1990. Vaccine 8:164–8.
58. Hsu, K-H L, M D Lubeck, A R Davis, R A Bhat et al. 1991. in Vaccines 91, 1991., Cold Spring Harbor Laboratory Press.
59. Kohler, G., Howe S. C., and Milstein, C., 1976. Eur. J. Immunol. 6:292–295.
60. Soman, G. Weltzin, R., Lee, C. K., Attardo, L., Mittler, E. S. and Monath, T., 1993. J. Immunol 150:116A.

I claim:

1. A monoclonal IgA antibody to Respiratory Syncytial Virus which is produced by hybridoma cell line HNK20 (ATCC accession number HB 11394).

2. A composition comprising a monoclonal antibody as claimed in claim 1 and a carrier or diluent.

3. Hybridoma cell line HNK20 (ATCC accession number HB 11394) which produces a monoclonal IgA antibody to Respiratory Syncytial Virus.

4. A composition comprising hybridoma cell line HNK20 (ATCC accession number HB 11394), which produces a monoclonal IgA antibody to Respiratory Syncytial Virus, and a nutrient medium capable of maintaining the cell line.

5. A kit comprising:

a first container containing a plastic substrate coated with the monoclonal IgA antibody which is produced by hybridoma cell line HNK20 (ATCC accession number HB 11394); and a second container containing a monoclonal IgA antibody to Respiratory Syncytial Virus which is produced by hybridoma cell line HNK20 (ATCC accession number HB 11394), to which antibody a radio label or enzyme label has been attached.

6. A kit according to claim 5, in which the plastics substrate is a polystyrene in the forms of beads, sticks, tubes or plates.

7. A method of detecting a Respiratory Syncytial Virus antigen in a sample, said method comprising the steps of:

(i). contacting said sample with the monoclonal IgA antibody produced by hybridoma cell line HNK20 (ATCC accession number HB 11394); and (ii). detecting said antibody bound to said sample as an indication of the presence of said antigen in said sample.

8. A method of diagnosing the presence of respiratory syncytial virus antigen in a biological sample, said method comprising the steps of:

contacting said biological sample with a monoclonal IgA antibody to Respiratory Syncytial Virus which is produced by hybridoma cell line HNK20 (ATCC accession number HB 11394); and detecting the presence of said antigen by:

(a). immunofluorescent microscopy; or (b). immuno-electron microscopy.

9. A method of diagnosing the presence of Respiratory Syncytial Virus antigen in a biological sample, said method comprising detecting the presence of said antigen by:

(a). a solid-phase radiometric assay comprising the steps of:

(i). providing a first monoclonal IgA antibody to Respiratory Syncytial Virus bound to a solid phase;

(ii). contacting said first monoclonal IgA antibody bound to said solid phase with said biological sample;

(iii). washing away the portion of said biological sample not bound to said first monoclonal IgA antibody bound to said solid phase;

(iv). contacting the reaction product of step (iii) with a second monoclonal IgA antibody to Respiratory Syncytial Virus tagged with a radiolabel; and (v). detecting said second monoclonal IgA antibody tagged with said radiolabel bound to said solid phase as a measure of the presence of said Respiratory Syncytial Virus antigen in said biological sample; or (b). an enzyme-linked immunoassay comprising the steps of:

(i). providing said first monoclonal IgA antibody to Respiratory Syncytial Virus bound to a solid phase;

(ii). contacting said first monoclonal IgA antibody bound to said solid phase with said biological sample;

(iii). washing away the portion of said biological sample not bound to said first monoclonal IgA antibody;

(iv). contacting the reaction product of step (iii) with a second monoclonal IgA antibody to Respiratory Syncytial Virus Tagged with an enzyme label;

(v). contacting the reaction product of step (iv) with the substrate of said enzyme label; and (vi). detecting the product formed in the reaction of step (v) as a measure of the presence of said Respiratory Syncytial Virus antigen in said biological sample;

wherein said first and second monoclonal IgA antibodies against Respiratory Syncytial Virus are produced by hybridoma cell line HNK20 (ATCC accession number HB 11394).

* * * * *

UNITED STATES PATENT AND TRADEMARK OFFICE
CERTIFICATE OF CORRECTION

PATENT NO.   : 5,534,411
DATED        : July 9, 1996
INVENTOR(S)  : Richard A. Weltzin It is certified that error appears in the above-identified patent and that said Letters Patent is hereby corrected as shown below:

Title page,
Item [54], replace "AMD" with -- AND --;
Item [21], replace "Appl. No.: 411,858" with -- Appl. No.: 08/411,858 --;
Item [56], References Cited, OTHER PUBLICATIONS,
Reference beginning with
"Norrby et al.," replace "lage" with -- large --;
Reference beginning with "Scott et al.," replace "nasopharygenal" with
-- nasopharyngeal --;
References beginning with -- Winner, III et al.," replace "Immunology" with
-- Immunity --;
References beginning with "Taylor et al.," replace begin a new line with the reference beginning with "Stott et al.";
References beginning with "Waldman," replace "Waldman" with -- Waldmann -- and "1657-1602" with -- 1602-1662 --;

Under OTHER PUBLICATIONS, in reference beginning with "Piazza et al.," delete "[\N]";

Column 1,
Line 11, replace "virus" with -- Virus --;

Column 3,
Line 52, replace "pharamaceutically" with -- pharmaceutically --;

Column 8,
Table 4, under Group 5, replace "iGA" with -- IgA --;

Column 12,
Line 54, delete the second "are";

Column 13,
Line 11, after "43:" insert -- 150-157. --;
Line 66, reference 37, replace "Yound" with -- Young --; and

UNITED STATES PATENT AND TRADEMARK OFFICE
CERTIFICATE OF CORRECTION

PATENT NO. : 5,534,411
DATED : July 9, 1996
INVENTOR(S) : Richard A. Weltzin

It is certified that error appears in the above-identified patent and that said Letters Patent is hereby corrected as shown below:

Column 14,
Line 48, reference 57, replace "Wt" with -- W T --.

Signed and Sealed this

Sixth Day of August, 2002

Attest:

JAMES E. ROGAN
Attesting Officer     Director of the United States Patent and Trademark Office